(12) United States Patent
Koh et al.

(10) Patent No.: US 11,740,756 B1
(45) Date of Patent: Aug. 29, 2023

(54) DISPLAY ADJUSTMENTS TO PROVIDE CUES FOR IMPROVED VIEWER POSTURE

(71) Applicant: International Business Machines Corporation, Armonk, NY (US)

(72) Inventors: Timothy Waileong Koh, Chuo-ku (JP); Yoshio Horiuchi, Hiratsuka (JP); Mayumi Goto, Ayase (JP); Sho Ayuba, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/660,273

(22) Filed: Apr. 22, 2022

(51) Int. Cl.
G06F 3/04815 (2022.01)
G16H 20/30 (2018.01)

(52) U.S. Cl.
CPC ......... *G06F 3/04815* (2013.01); *G16H 20/30* (2018.01)

(58) Field of Classification Search
CPC ............................ G06F 3/04815; G16H 20/30
See application file for complete search history.

(56) References Cited

U.S. PATENT DOCUMENTS

| | | | |
|---|---|---|---|
| 10,453,373 B2 | 10/2019 | Moeller | |
| 11,544,865 B1* | 1/2023 | Kurz | G06T 7/73 |
| 2003/0080979 A1* | 5/2003 | Satoh | G06F 3/012 |
| | | | 345/633 |
| 2010/0220897 A1* | 9/2010 | Ueno | H04N 7/15 |
| | | | 382/115 |
| 2011/0172564 A1* | 7/2011 | Drew | A61B 5/061 |
| | | | 600/587 |
| 2021/0397250 A1* | 12/2021 | Akgul | G06F 3/012 |
| 2022/0100992 A1* | 3/2022 | Ran | G06V 40/23 |
| 2022/0300120 A1* | 9/2022 | Nishibe | G06F 3/04815 |
| 2022/0327714 A1* | 10/2022 | Cook | G06T 7/70 |

FOREIGN PATENT DOCUMENTS

CN 110750156 A 2/2020

OTHER PUBLICATIONS

"Lumo Lift", Feelpeak, Downloaded from the Internet on Jan. 14, 2022, 11 pgs.,<https://feelpeak.com/lumo-lift/>.
"Upright Go", Downloaded from the Internet on Jan. 14, 2022, 9 pgs., © Upright 2022, <https://www.uprightpose.com>.
Disclosed Anonymously, "A Method for Adjusting the User's Posture While Using a Digital Device by Adjusting the Screen Content in Real-Time", An IP.com Prior Art Database Technical Disclosure, IP.com No. IPCOM000263522D, Sep. 7, 2020, 6 pgs.
Elnaffar, et al., "An App Approach to Correcting the Posture of Smartphone Users", ResearchGate, Feb. 2018, 5 pgs., DOI: 10.1109/ICASET.2018.8376910.

* cited by examiner

*Primary Examiner* — Jitesh Patel
(74) *Attorney, Agent, or Firm* — David B. Woycechowsky

(57) ABSTRACT

A display frame position/orientation adjustment is made to a computer display data set before it is displayed on a display screen (for example, a display screen of a user's smartphone). The offsets the display from the display frame defined by the edges of the display screen. The user tends to counter these offsets by moving from a relatively poor body posture and into a good body posture.

18 Claims, 5 Drawing Sheets

DISPLAY ADJUSTMENTS TO PROVIDE CUES FOR IMPROVED VIEWER POSTURE

BACKGROUND

The present invention relates generally to the field of posture correction software implemented through smart phones, virtual reality goggles and the like.

U.S. Patent Application Publication US 2018/0190175 ("Moeller") states as follows: "Altering a display of visual information in real time on an electronic visual display of a mobile computing system to encourage desirable behavior, such as spinal posture. In an embodiment, a system determines an angle of inclination of a mobile computing system, which is indicative of a spinal posture of a user of the system. When the user's spinal posture is within an angular range that corresponds to a less desirable spinal posture, the system progressively alters a display of visual information by an electronic visual display of the system to encourage the user toward a more desirable spinal posture. . . . In an embodiment, altering the display includes displaying a non-disruptive frame around the visual information to note less desirable spinal posture and affirm more desirable spinal posture. In another embodiment, altering the display includes progressively obfuscating the visual information to prevent effective use of the device with less desirable spinal posture . . . processor sets the opacity of an overlay screen to zero percent (i.e., the overlay screen is one hundred percent transparent). In an embodiment, the overlay screen is a gray screen, as described more fully hereinafter. In another embodiment, the overlay screen is any image desired by the user (e.g., a "Devolution of Man" image, etc.). [One of the drawings of Moeller] illustrates an exemplary embodiment in which the overlay screen has an opacity of zero percent when the angle of inclination of system is 77 degrees. In this exemplary embodiment, the overlay screen has an opacity of zero percent when the angle of inclination of system 100 is between 90 degrees and 76 degrees. . . . Although embodiments described herein include obfuscation of 100% of the total area of visual information, embodiments in which about 25% or more (i.e., less than 100%) of the total area of visual information is obfuscated are within the scope of the present disclosure. [E]mbodiments in which less than 100% of the total area of visual information is obfuscated. For example, frame (a) illustrates about 25% obfuscation, frame (b) illustrates about 50% obfuscation, and frame (c) illustrates about 75% obfuscation. In the embodiments utilizing less than 100% obfuscation, the area of obfuscation may be located at any position within the area of visual information. For example, the area of obfuscation may be located directly in the center of the area of visual information, along one or more sides of the area of visual information, based on importance of the underlying visual information (e.g., the obfuscation is placed atop visual information having higher importance to the user, etc.), or the like. Moreover, the area of obfuscation may be discontinuous (e.g., stripes, chevron pattern, polka-dot, etc.) such that areas of obfuscation are interwoven with areas of visual information." (reference numerals omitted)

SUMMARY

According to an aspect of the present invention, there is a method, computer program product and/or system that performs the following operations (not necessarily in the following order): (i) receiving a body position data set including information indicative of a set of body position attribute value(s) corresponding to a set of body position attribute(s) of a user; (ii) determining that the first attribute value of the set of body position attribute values indicates a relatively poor posture; (iii) receiving an original version of a first display data set including information indicative of a visual display to be displayed to the user within a display frame on a display screen of a display device; (iv) adjusting a display frame position/orientation of the original version of the first display data set to obtain an adjusted first display data set, so that the adjustment of the display frame position orientation will tend to cause the user to move from the relatively poor posture position to an improved posture position; and (v) displaying on the display screen of the display device a visual display corresponding to the adjusted first display data set.

DETAILED DESCRIPTION

Figure 1:
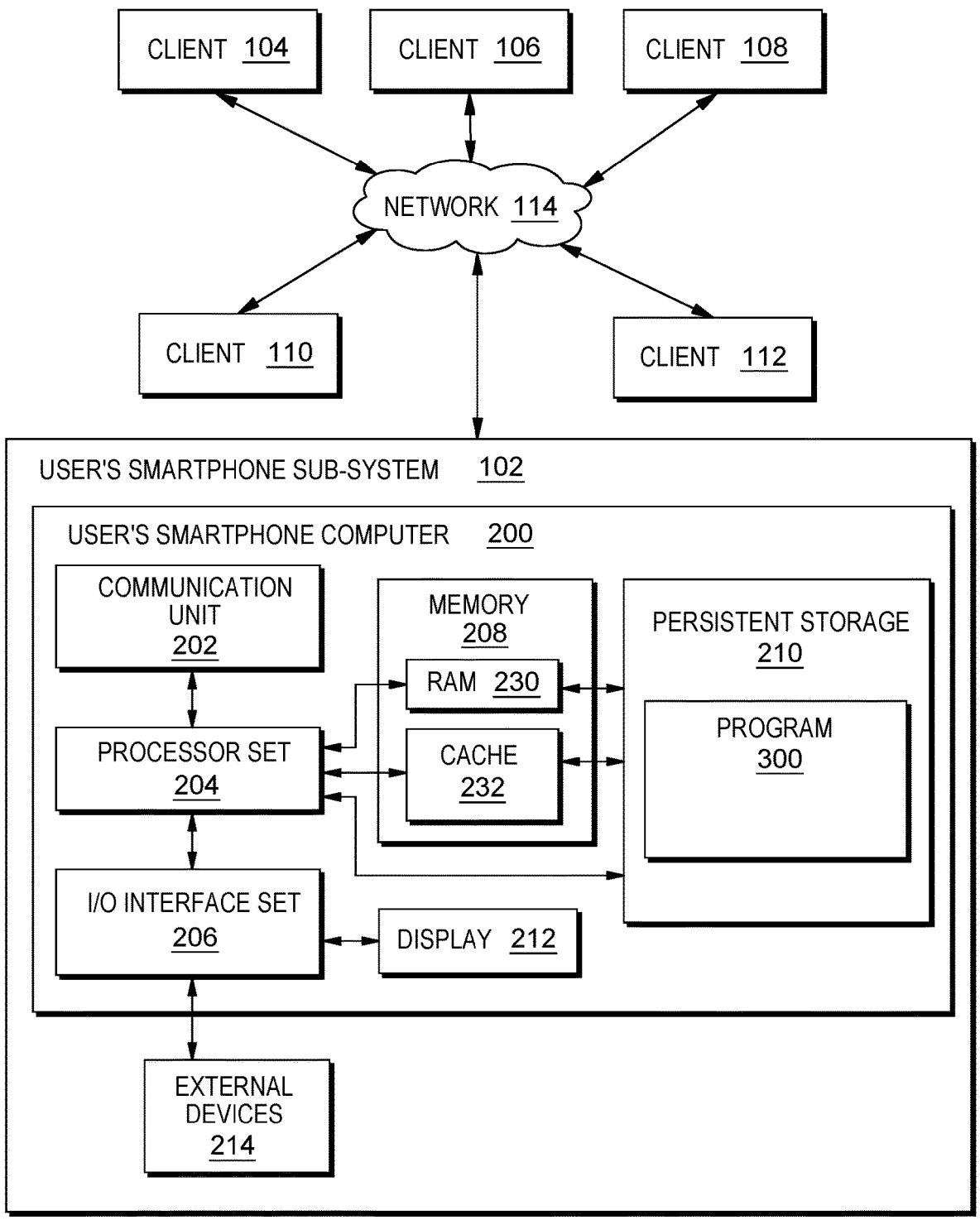
FIG. 1 is a block diagram of a first embodiment of a system according to the present invention.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product at any possible technical detail level of integration. The computer program product may include a computer readable storage medium (or media) having computer readable program instructions thereon for causing a processor to carry out aspects of the present invention. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention. Networked computers system 100 includes: user's smartphone subsystem 102 (sometimes herein referred to, more simply, as subsystem 102); client subsystems 104, 106, 108, 110, 112; and communication network 114. User's smartphone subsystem 102 includes: user's smartphone 200; communication unit 202; processor set 204; input/output (I/O) interface set 206; memory 208; persistent storage 210;

display 212; external device(s) 214; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with user's smartphone 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
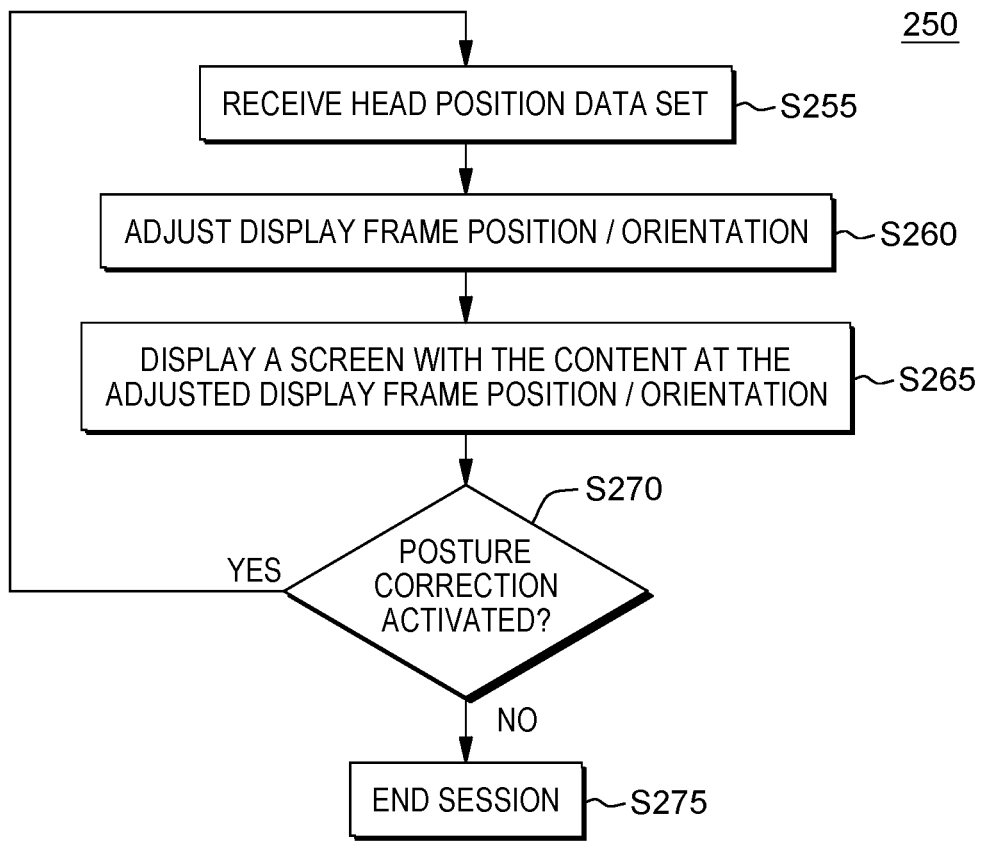
FIG. 2 is a flowchart showing a first embodiment method performed, at least in part, by the first embodiment system.
Figure 3:
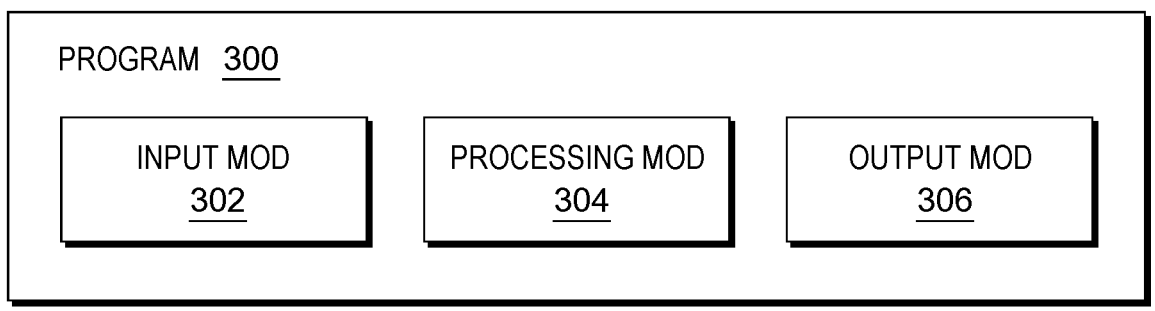
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2 and 3.

Processing begins at operation S255, where, after activation of the posture correction feature on user's smartphone 200, input module ("mod") 302 receives user's head position data set. The user's head position data set includes information indicative of the position and/or angular orientation of the user's head. In this embodiment, the head position is: (i) based exclusively from video images collected by a camera built into the user's smartphone; and (ii)

calculated by a separate program, based on the video images, which is also included in the smartphone (but not separately shown in FIG. 1). Alternatively or additionally, and as discussed in the next sub-section of this Detailed Description section, other types of input data (for example, accelerometer data) could be as a basis for the calculation of head position. The program for calculating head position may reside in whole or in part at locations remote from the user's smartphone (for example, client subsystem 102).

In this embodiment, the head position data includes three attributes as follows: (i) forward head tilt (see FIG. 4A); (ii) lateral head tilt (see FIG. 5A); and (iii) face-to-screen distance (see FIG. 6A). It is noted that forward head tilt and lateral head tilt are measured relative to the ground, but the face-to-screen distance is a relative distance between the user's face and the user's smartphone. In other words, head position may be measured, in various embodiments of the present invention, with respect to different physical frames of reference.

Processing proceeds to operation S260, where processing mod 304 adjusts a "display frame position/orientation" in a manner that encourages the user to move into a better posture. In embodiments with head and/or neck mounted equipment, the posture correction that is being encouraged would primarily involve head and neck movements so that the users head and neck are appropriately straight, vertical and upright. On the other hand, in embodiments involving a display on a handheld mobile phone, display adjustments of the present invention will tend to cause the user to move their arm so that the mobile phone is held in a different position with respect to the user's body, and this in turn will cause the user to adjust their back, head and or neck into a better posture. For example, in some embodiments, the user is holding the mobile phone too low with respect to their shoulders. In these embodiments, by shifting the display upwards on the display device, the user is encouraged to raise their arm, which causes the user's head to tilt backwards into a straighter and more correct posture.

As the term is used herein, display frame position/orientation refers to any positional and/or orientational offsets between: a display corresponding to a computer display dataset positioned and oriented relative to the display screen without adjustment; and a display that has been adjusted in position and/or orientation relative to the display screen. The computer display data set is adjusted for display frame/orientation offset to yield an adjusted computer display data set. The following three (3) paragraphs will go through the following three examples: (i) upwards direction positional offset to counter frontwards head tilt; (ii) rotational direction orientational offset (within the plane of the display screen) to counter lateral head tilt; and (iii) z-axis (that is, direction perpendicular to the plane of the display screen) direction positional offset, thereby making the content of the display (for example, text in the display) appear larger to counter a condition where the display screen is being held to close to the user's face (that is, the facial portion of the user's head).

Figure 4A:
FIGS. 4A, 4B and 4C are screenshot views generated by the first embodiment system.
Figure 4B:
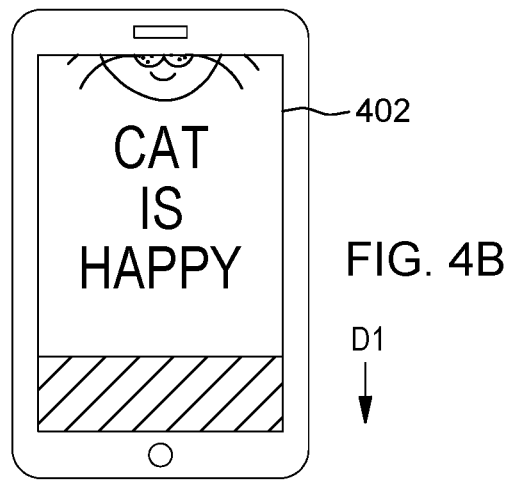
Figure 4C:
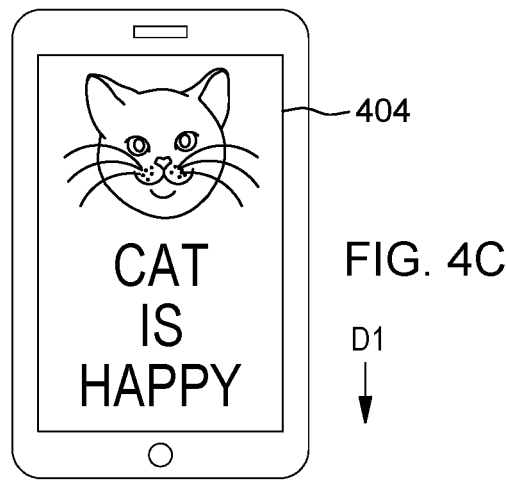

One type of posture correction triggered by this embodiment is forward/backward head tilt (herein sometimes referred to as forward head tilt). As shown in FIG. 4A, inside view 400 of the user, forward-backward head tilt is rotation in the direction of arrow R1, roughly centered about a point in the user's neck at their spine. In this example, the user's head is tilted too far forward to be consistent with good posture. As a response, an upwards adjustment is made to the display frame position/orientation for a display data set that will be displayed to the user. As shown by comparing screen shot 402 of FIG. 4B with screenshot 404 of FIG. 4C, the display data set is adjusted in the counter D1 direction. The reason for this adjustment is that the user will tend to counter visual presented under the display frame position/orientation adjustment by tilting the head upwards (in the R1 direction) into a position consistent with good posture. Screenshot 404 of FIG. 4C shows the display presented in a subsequent cycle to the user after the user has tilted their head upwards to achieve good posture, meaning that there is no display frame adjustment, and the display is relative to the display screen as originally intended. In this example, the offset is directly proportional to the amount of the user's excessive forward head tilt. In other embodiments, and as discussed in the next sub-section of this Detailed Description section, the offset with respect to the display frame may be gradually introduced over time, so that the degree of pressure assumes a correct posture is applied progressively.

Figure 5A:
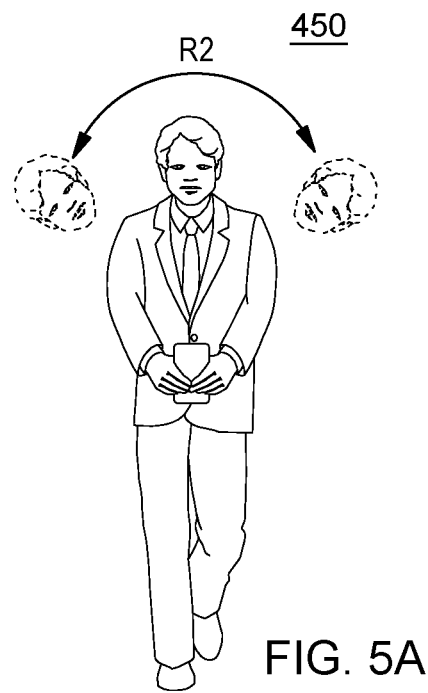
FIGS. 5A, 5B and 5C are screenshot views generated by the first embodiment system.
Figure 5B:
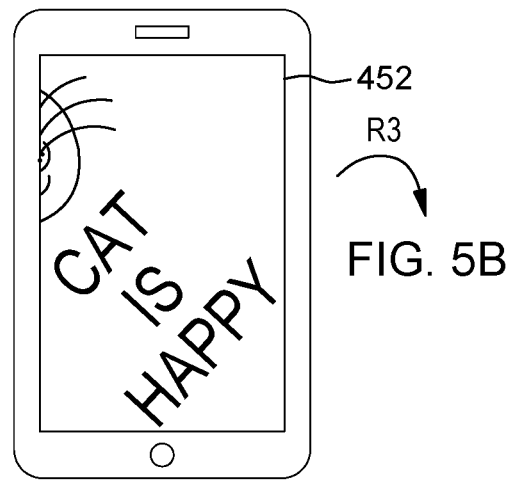
Figure 5C:
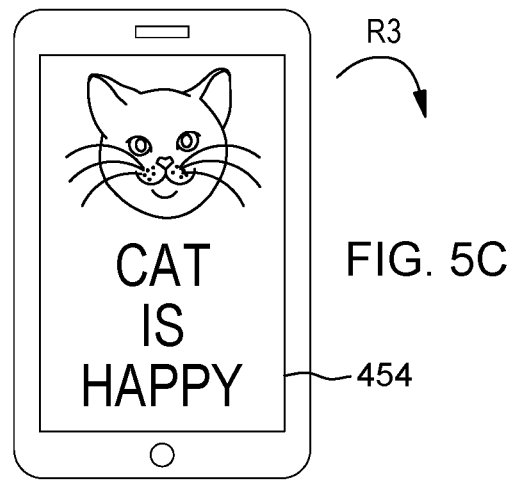

Another type of posture correction triggered by this embodiment is lateral head tilt. As shown in FIG. 5A, in front view 450 of the user, lateral head tilt is rotation in the direction of arrow R2, again, roughly centered about a point in the user's neck at their spine. In this example, the user's head is tilted too far laterally to be consistent with good posture. As a response, an upwards adjustment is made to the display frame position/orientation for a display data set that will be displayed to the user. As shown by comparing screen shot 452 of FIG. 5B with screenshot 454 of FIG. 5C, the display data set is adjusted in the R3 rotational direction. The reason for this adjustment is that the user will tend to counter visual presented under the display frame position/orientation adjustment by tilting the head toward a straight up vertical position (that is, to pivot towards the R3 direction) into a position consistent with good posture. Screenshot 454 of FIG. 5C shows the display presented in a subsequent cycle to the user after the user has tilted their head to a straight up position to achieve good posture, meaning that there is no display frame adjustment, and the display is oriented relative to the display screen as originally intended. In this example, the rotational offset is directly proportional to the amount of the user's excessive lateral head tilt. Alternatively, the rotational offset could be progressively applied over time.

Figure 6A:
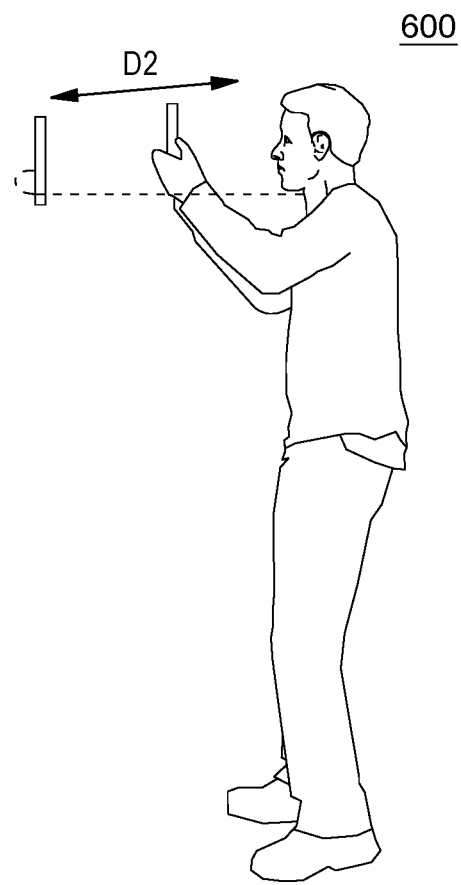
FIGS. 6A, 6B and 6C are screenshot views generated by the first embodiment system.
Figure 6B:
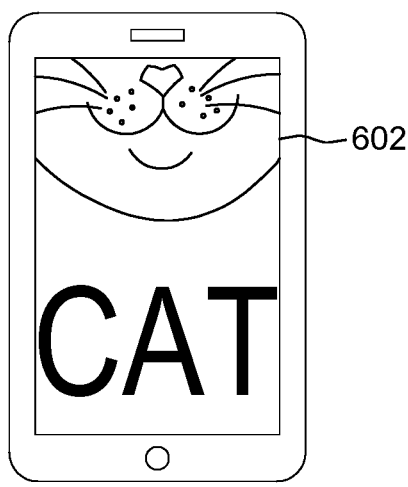
Figure 6C:
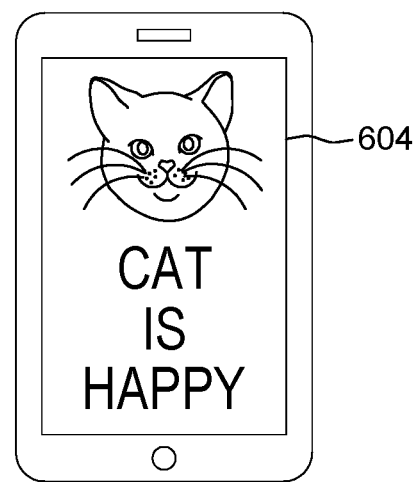

Another type of posture correction triggered by this embodiment is the condition of a user's face being too close to the screen. As shown in FIG. 6A, inside view 600 of the user, the distance between the user's face and the display screen is measured along linear axis D2. In this example, the user's head (that is, their face) is located to close to the screen to be consistent with good posture. As a response, a z-axis adjustment (that is a translational adjustment in the direction perpendicular to the plane of the display screen) is made to the display frame position/orientation for a display data set that will be displayed to the user. As shown by comparing screen shot 602 of FIG. 6B with screenshot 604 of FIG. 6C, the display data set is adjusted so that the content of the display appears closer to the plane of the display screen, so that only a small part of the content is visible in the display frame and the visible portion of the content is magnified. The reason for this adjustment is that the user will tend to counter visual presented under the display frame position/orientation adjustment by increasing the D2 axis distance between face and display screen to move into a position consistent with good posture. Screenshot 604 of FIG. 6C shows the display presented in a subsequent cycle to the user after the user has tilted their head to a straight up position to achieve good posture, meaning that there is no display frame adjustment, and the display is positioned relative to the display screen along the z-axis as originally intended. In this example, the rotational offset is directly proportional to the amount of the user's excessive facial proximity to the display screen. Alternatively, the positional offset could be progressively applied over time. This embodiment checks for three body position attributes that indicate bad posture. Other embodiments may account for more, or fewer attributes of the user's body position. Alternatively or additionally, different body position attributes than the three used in this example.

Processing proceeds to operation S265, where output mod 306 causes the adjusted display data set (corresponding to FIGS. 4B, 5B and 6B) to be displayed on display 212 of user's smartphone 200.

Processing proceeds to operation S270, where processing mod 304 determines whether the posture correction feature is still activated on user's smartphone 200. If it is, the processing loops back to operation S255, to begin again with updated information on the user's changing head position. If the posture correction feature is no longer activated, the processing proceeds to operation S275, where the posture correction session is ended.

III. Further Comments and/or Embodiments

Some embodiments of the present invention recognize one, or more, of the following facts, potential problems and/or potential areas for improvement with respect to the current state of the art: (i) when using a smartphone, it is easy for a user to fall into the trap of leaning their head forwards to look down at the smartphone display; (ii) this puts a lot of strain on the user's neck and back muscles and results in a poor posture; (iii) the correct posture would be to hold the smartphone level with your eyes and not below which would cause bad posture; and/or (iv) if there was a way to alert the smartphone user in a non-disruptive way to improve their posture, this problem can be addressed.

Some embodiments of the present invention may include one, or more, of the following operations, features, characteristics and/or advantages: (i) computer technology to address the poor posture while using a smartphone; (ii) detection of poor posture using sensors on the smartphone (GPS (global positioning system), accelerometer, gyro, camera, etc.) to determine the height, closeness to the face and angle of the phone (using existing technologies and/or posture detection technologies to be developed in the future); and/or (iii) interacts with the user in a non-disruptive way to encourage proper posture.

A method for smart phone and/or VR (virtual reality) based posture correction will now be set forth: (i) when the smartphone is not held at eye level and is too low, then the contents of the screen will shift upwards as a virtual screen floating above the top border of the physical phone and will gradually become difficult to see until the physical phone is moved upwards to match the screen with the rising virtual screen so it is back to normal eye level; (ii) this will result in the user having a tendency to naturally restore their correct posture without thinking; (iii) in addition to the shifting of the screen, if the screen is too close to the face, then the contents of the screen will be enlarged based on how close the phone is to the face (that is, the closer it is to the face, the larger it will display, which will encourage the user to move their face away, as they move their head backwards, the enlarged contents will return back to the normal size); (iv) blurring of the screen can also help with this and can be used instead of or in combination with the enlarging of the screen; and (v) using a combination of the foregoing techniques will result in the user, themselves, correcting their posture without consciously thinking about it—this is a potential benefit of this method over using vibrations or messages to bother the user.

Some embodiments of the present invention may include one, or more, of the following operations, features, characteristics and/or advantages: (i) the posture correction techniques can be calibrated to the user and it can be set as a very gradual unnoticeable level where the posture is slowly improved with the least disruption, or it can be set to be quite aggressive and have more disruption to the user experience; (ii) if the screen raises too quickly and the user does not move their phone or perform the correction to follow it, then the aggressiveness of the correction techniques applied can be reduced to allow the user to gradually adjust their posture; (iii) a friendly reminder though a vibration and enlarging of the screen can be set using a threshold if the correction techniques are ignored for too long; (iv) the technologies described also apply to other scenarios such as using a VR headset and correcting posture; (v) if a user is in a VR application and is standing with incorrect posture for a period of time, then they can be encouraged to stand up straight with the same techniques of having the screen shift upwards and having to follow the moving screen so that the head is upright and at the right height for a correct posture; and/or (vi) if the head is too far forward, the scene can blur until the head is moved backwards.

Figure 7:
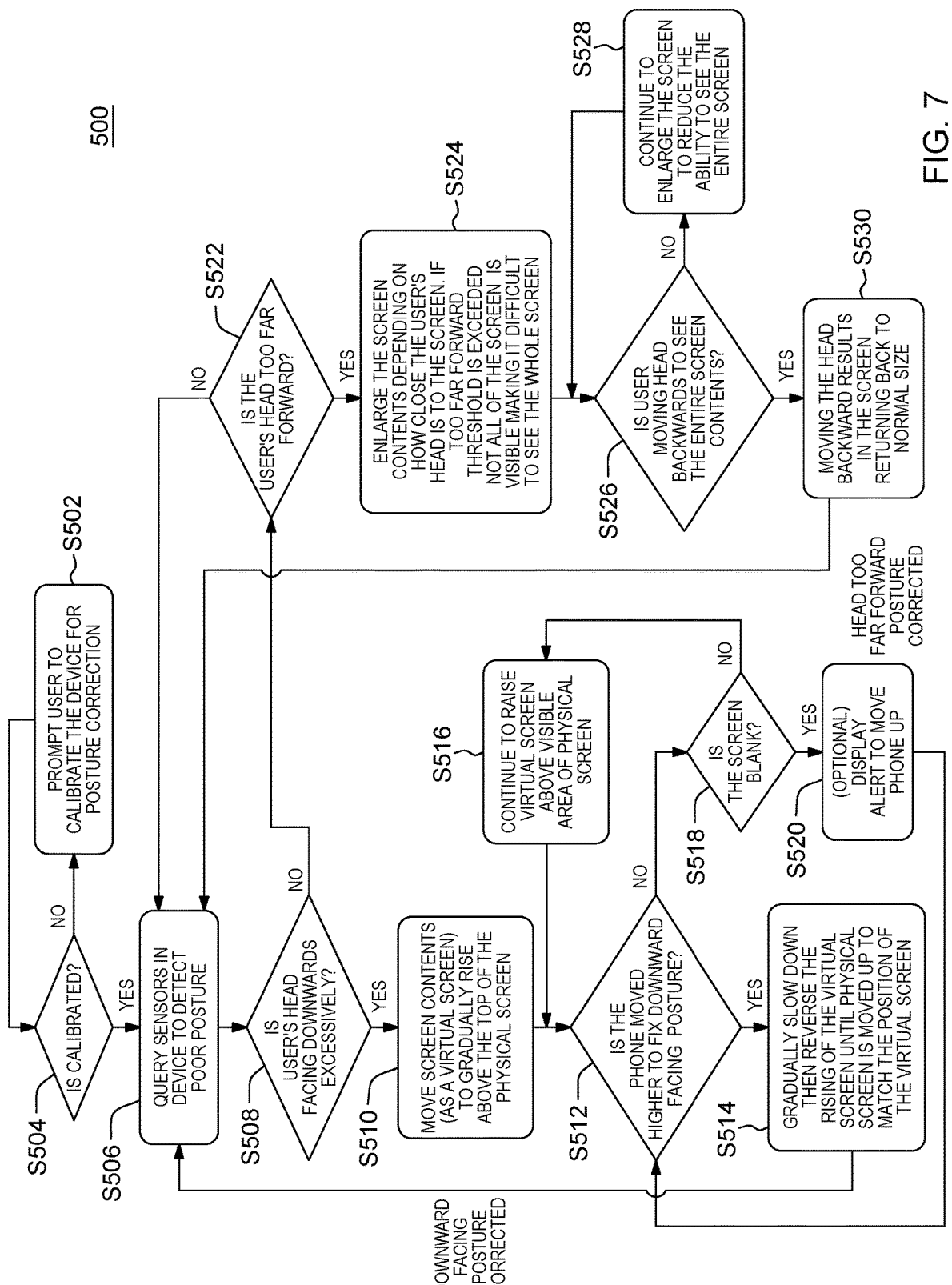
FIG. 7 a flowchart showing a second embodiment of a method according to the present invention.

As shown in FIG. 7, flowchart 500 includes the following operations (with process flow among and between the operations as shown by arrows in FIGS. 7): S502; S504; S506; S508; S510; S512; S514; S516; S518; S520; S522; S524; S526; S528; and S530.

A method for collecting posture of a smartphone and/or VR headset user includes the following operations: (i) detecting whether (A) user's head facing downwards or (B) the user's head too far forward to the smartphone; (ii) in response to detection of alternative (A), moving screen contents as a virtual screen to gradually rise above the top of the physical screen; (iii) when physical screen is moved up to match the position of the virtual screen, reversing the rising of the virtual screen; (iv) in response to detection of alternative (B), enlarging and/or obscuring the screen contents depending on how close the user's head is to the screen; and (v) when the user moves head backwards, un-enlarging and/or un-obscuring the screen contents depending on how far the user's head is to the screen. Some embodiments may include the following operation: if the physical screen is blank, displaying an alert to move the smartphone up.

Some embodiments of the present invention may include one, or more, of the following operations, features, characteristics and/or advantages: (i) calibrating the posture correction techniques to the user and setting them at a very gradual unnoticeable level, wherein the posture is slowly improved with the least disruption, or it can be set to be quite aggressive and have more disruption to the user experience; (ii) if the screen raises too quickly and the user does not move their phone or perform the correction to follow it, reducing the aggressiveness of the correction techniques applied, to allow the user to gradually adjust their posture; (iii) compatible with any VR devices; (iv) non-disruptive and encourages the correction of the user's posture and device position by having the user unconsciously follow the virtual screen guiding the device upwards; (v) has the user unconsciously follow the virtual screen guiding the device upwards; and/or (vi) encourages the correction of the user's posture and device position by having the user unconsciously follow the virtual screen guiding the device upwards.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

And/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

Set of thing(s): does not include the null set; "set of thing(s)" means that there exist at least one of the thing, and possibly more; for example, a set of computer(s) means at least one computer and possibly more.

Virtualized computing environments (VCEs): VCEs can be stored as "images." A new active instance of the VCE can be instantiated from the image. Two types of VCEs are virtual machines and containers. A container is a VCE that uses operating-system-level virtualization. This refers to an operating system feature in which the kernel allows the existence of multiple isolated user-space instances, called containers. This isolated user-space instances may look like real computers from the point of view of programs running in them. A computer program running on an ordinary operating system can see all resources (connected devices, files and folders, network shares, CPU power, quantifiable hardware capabilities) of that computer. However, programs running inside a container can only see the container's contents and devices assigned to the container.

Cloud computing system: a computer system that is distributed over the geographical range of a communication network(s), where the computing work and/or computing resources on the server side are primarily (or entirely) implemented by VCEs (see definition of VCEs in previous paragraph). Cloud computing systems typically include a cloud orchestration module, layer and/or program that manages and controls the VCEs on the server side with respect to instantiations, configurations, movements between physical host devices, terminations of previously active VCEs and the like.

What is claimed is:

1. A computer-implemented method (CIM) comprising:
receiving a body position data set including information indicative of a set of body position attribute value(s) corresponding to a set of body position attribute(s) of a user;
determining that the first attribute value of the set of body position attribute values indicates a relatively poor posture;
receiving an original version of a first display data set including information indicative of a visual display to be displayed to the user within a display frame on a display screen of a display device;
adjusting a display frame position/orientation of the original version of the first display data set to obtain an adjusted first display data set, so that the adjustment of the display frame position orientation will tend to cause the user to move from the relatively poor posture position to an improved posture position; and
displaying on the display screen of the display device a visual display corresponding to the adjusted first display data set.

2. The CIM of claim 1 wherein the display device is built into a smartphone.

3. The CIM of claim 1 wherein the display device is built into a virtual reality (VR) headset.

4. The CIM of claim 1 wherein the first attribute is forward head tilt and display frame position/orientation is adjusted to create an upwards offset.

5. The CIM of claim 1 wherein the first attribute is face to screen distance and display frame position/orientation is adjusted along an axis perpendicular to a plane of the display screen.

6. The CIM of claim 1 wherein the display frame position adjustment creates an offset in an upwards linear direction that is countered by the user moving and/or rotating their head upwards toward a straight up vertical position.

7. A computer program product (CPP) comprising:
a set of storage device(s); and
computer code stored collectively in the set of storage device(s), with the computer code including data and instructions to cause a processor(s) set to perform at least the following operations:
receiving a body position data set including information indicative of a set of body position attribute value(s) corresponding to a set of body position attribute(s) of a user,
determining that the first attribute value of the set of body position attribute values indicates a relatively poor posture,
receiving an original version of a first display data set including information indicative of a visual display to be displayed to the user within a display frame on a display screen of a display device,
adjusting a display frame position/orientation of the original version of the first display data set to obtain an adjusted first display data set, so that the adjustment of the display frame position orientation will tend to cause the user to move from the relatively poor posture position to an improved posture position, and displaying on the display screen of the display device a visual display corresponding to the adjusted first display data set.

8. The CPP of claim 7 wherein the display device is built into a smartphone.

9. The CPP of claim 7 wherein the display device is built into a virtual reality (VR) headset.

10. The CPP of claim 7 wherein the first attribute is forward head tilt and display frame position/orientation is adjusted to create an upwards offset.

11. The CPP of claim 7 wherein the first attribute is face to screen distance and display frame position/orientation is adjusted along an axis perpendicular to a plane of the display screen.

12. The CPP of claim 7 wherein the display frame position adjustment creates an offset in an upwards linear direction that is countered by the user moving and/or rotating their head upwards toward a straight up vertical position.

13. A computer system (CS) comprising:
a processor(s) set;
a set of storage device(s); and
computer code stored collectively in the set of storage device(s), with the computer code including data and instructions to cause the processor(s) set to perform at least the following operations:
receiving a body position data set including information indicative of a set of body position attribute value(s) corresponding to a set of body position attribute(s) of a user,
determining that the first attribute value of the set of body position attribute values indicates a relatively poor posture,
receiving an original version of a first display data set including information indicative of a visual display to be displayed to the user within a display frame on a display screen of a display device,
adjusting a display frame position/orientation of the original version of the first display data set to obtain an adjusted first display data set, so that the adjustment of the display frame position orientation will tend to cause the user to move from the relatively poor posture position to an improved posture position, and
displaying on the display screen of the display device a visual display corresponding to the adjusted first display data set.

14. The CS of claim 13 wherein the display device is built into a smartphone.

15. The CS of claim 13 wherein the display device is built into a virtual reality (VR) headset.

16. The CS of claim 13 wherein the first attribute is forward head tilt and display frame position/orientation is adjusted to create an upwards offset.

17. The CS of claim 13 wherein the first attribute is face to screen distance and display frame position/orientation is adjusted along an axis perpendicular to a plane of the display screen.

18. The CS of claim 13 wherein the display frame position adjustment creates an offset in an upwards linear direction that is countered by the user moving and/or rotating their head upwards toward a straight up vertical position.

* * * * *